United States Patent [19]

Muller

[11] Patent Number: 4,959,067
[45] Date of Patent: * Sep. 25, 1990

[54] MANUAL SURGICAL SEPARATOR STRUCTURE AND METHOD

[75] Inventor: George H. Muller, Ann Arbor, Mich.

[73] Assignees: Joseph J. Berke, Detroit; A.I.R. Foundation, Ann Arbor, both of Mich. ; a part interest

[*] Notice: The portion of the term of this patent subsequent to Dec. 1, 2004 has been disclaimed.

[21] Appl. No.: 117,051

[22] Filed: Nov. 5, 1987

Related U.S. Application Data

[63] Continuation-in-part of Ser. No. 582,971, Nov. 21, 1983, Pat. No. 4,709,697.

[51] Int. Cl.⁵ ............................................. A61B 17/00
[52] U.S. Cl. ........................................ 606/190; 128/20
[58] Field of Search ................ 128/341, 357, 20, 303; 433/141; 606/190, 201, 204

[56] References Cited

U.S. PATENT DOCUMENTS

| | | | |
|---|---|---|---|
| 735,400 | 8/1903 | McCully | 128/303 R |
| 3,525,339 | 8/1970 | Halligan | 128/303 R |
| 3,547,103 | 12/1970 | Cook | 128/303 R |
| 4,357,940 | 11/1982 | Muller | 128/303 R |
| 4,709,697 | 12/1987 | Muller | 128/303 R |

FOREIGN PATENT DOCUMENTS 48504  4/1985  United Kingdom ................ 128/341

Primary Examiner—John D. Yasko

[57] ABSTRACT

Surgical separator structure comprising an elongated shaft having a handle at one end and a stem with controlled flexibility at the other end and a tissue separating tip secured to the other end of the flexible stem. The shaft may have a separate handle part and stem part secured together centrally of the shaft. The tip is preferably spherical and may be constructed to snap on the end of the stem and may also be retained by adhesive or the like. Alternatively, the other end of the stem may be molded into the tip to secure the tip to the stem. In the method of manufacture of the surgical separator, the handle and stem may be separately produced and secured together by a threaded connection while the tip may be snapped over the end of the stem and/or secured thereto with adhesive. Alternatively, the stem may be molded of "ABS" within a recess in the "TEFLON" tip to lock the tip on the stem. The handle is preferably color coded to provide a visual indication of the flexibility of the shaft. The tip is preferably colored a color contrasting to the color of the stem and tissue such as bright yellow and is preferably luminescent.

19 Claims, 2 Drawing Sheets

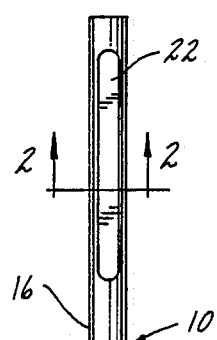
FIG. 1
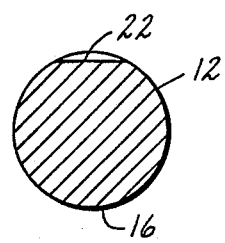
FIG. 2
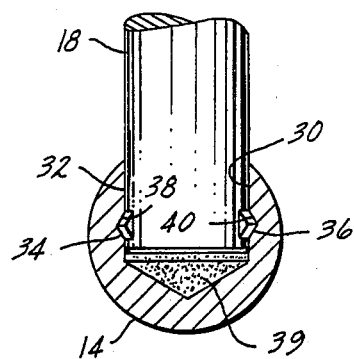
FIG. 3
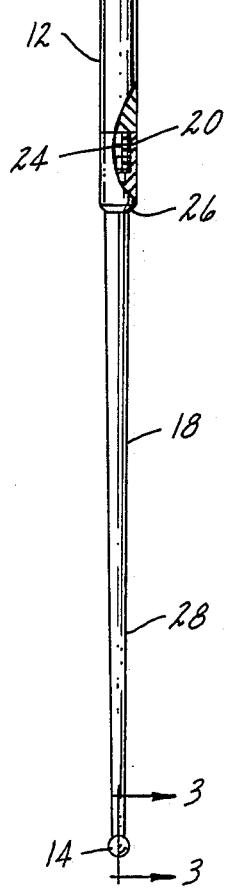
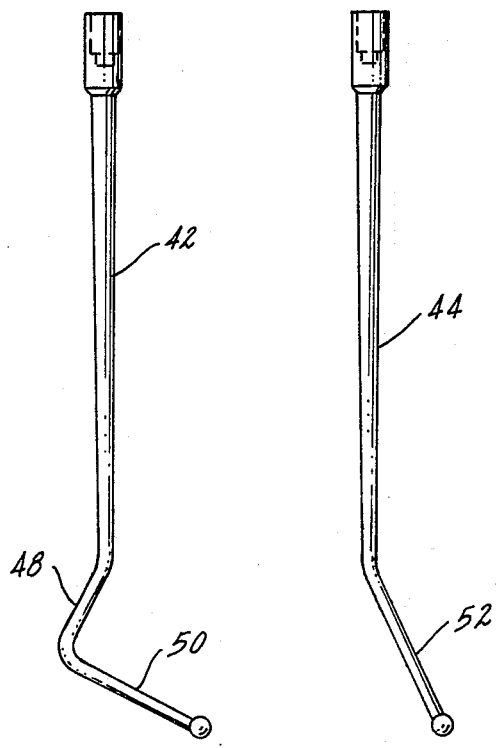
FIG. 4  FIG. 5
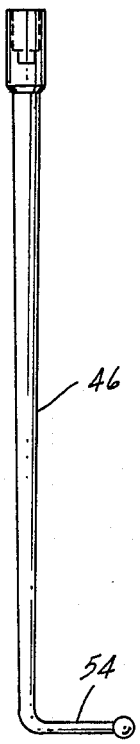
FIG. 6

FIG. 7
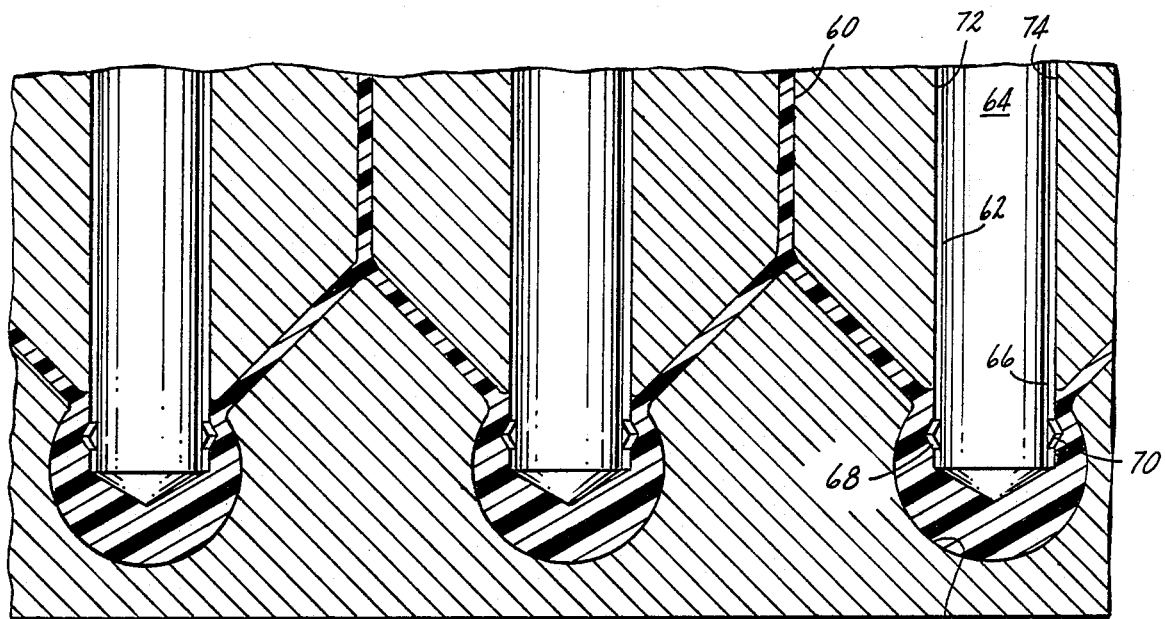
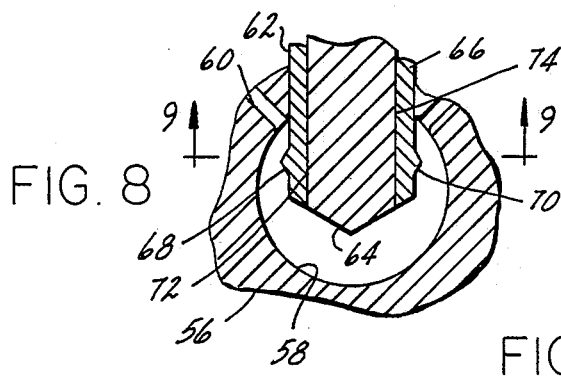
FIG. 8
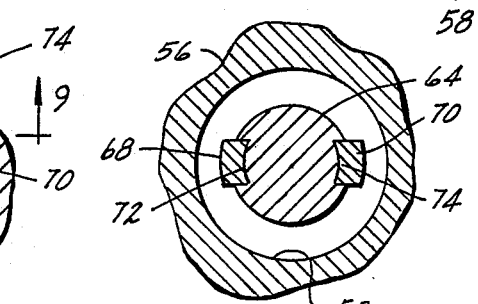
FIG. 9
FIG. 10
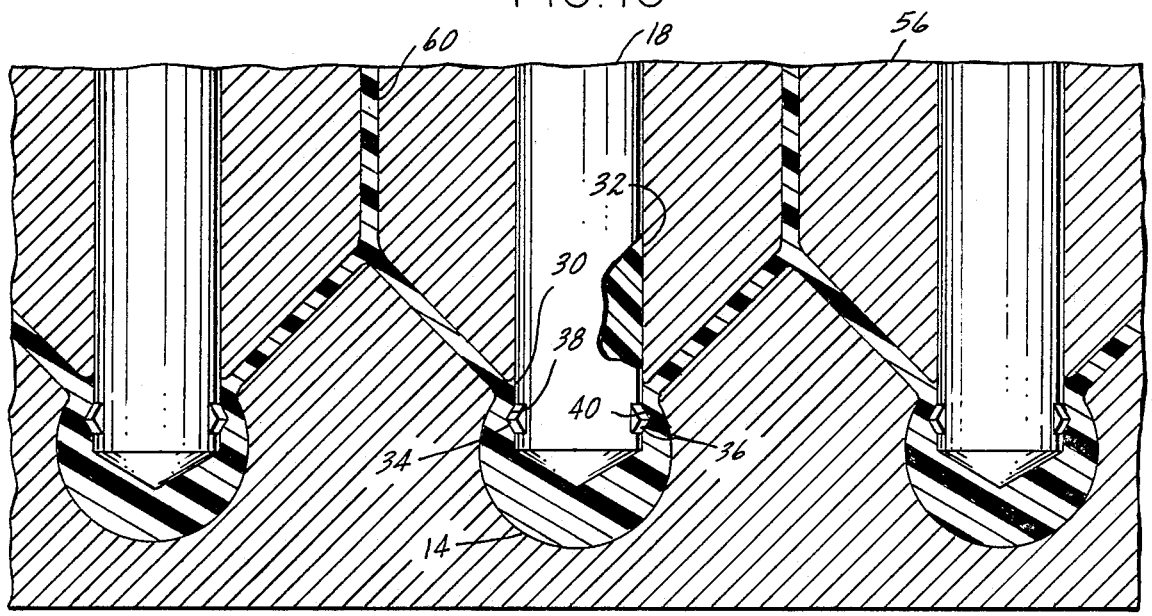

4,959,067

MANUAL SURGICAL SEPARATOR STRUCTURE AND METHOD

RELATION TO CORRESPONDING APPLICATION

This application is a continuation-in-part of Application Ser. No. 582,971 filed Nov. 21, 1983 now U.S. Pat. No. 4,709,697.

BACKGROUND OF THE INVENTION

1. Field of the Invention

The invention relates to surgical separating structures and methods and refers more specifically to a surgical separator or nudger including an elongated shaft having a handle section at one end thereof and a flexible stem at the other end with a working tip for separating or nudging tissue apart secured to the flexible stem at the other end of the shaft which may be produced by molding the tip, subsequently molding the flexible stem with the other end thereof in the tip to secure the stem and tip together and removably securing the handle to the stem. Alternatively, the handle and stem of the separating structure may be integrally molded as a single item.

In use, the surgical separator structure of the invention is utilized to nudge tissue with the tip thereof with the surgeon holding the handle so that when too much pressure is applied the tip of the surgical separator on the flexible stem will yield and deflect to prevent injury to tissue being separated and to provide a tactile and visual indication of the application of too much pressure in separating the tissue.

2. Description of the Prior Art

In the past, surgical tissue separation has been accomplished primarily with a scapel or scissors by cutting through the tissue or with very rigid metallic forceps by pushing and tearing tissue away. In many instances, it is possible to separate layers of tissue with less trauma to the tissue and more accurately with a surgical tissue separator that does not tear, sever or crush the tissue.

SUMMARY OF THE INVENTION

In accordance with the invention, a surgical tissue separator is provided which includes an elongated shaft having a handle section at one end and a flexible stem at the other end and a tip on the flexible stem. The flexible stem may have a plurality of different configurations such as straight, double bend, single bend and right angle working end.

The generally spheroidal tip of the surgical separator located at the outer extremity of the stem working end of the invention is spherical and may be provided with a locking recess for receiving the working end of the flexible stem. The tip may be secured to the flexible stem by projections on the stem and recesses in the tip with the tip being snapped over the end of the stem thus creating an interference fit and in addition being optionally adhered to the stem. Alternatively, the stem may be molded into a pre-molded tip to secure the top to the stem or the tip may be molded around a pre-molded stem.

In use, the surgical tissue separator or nudger of the invention may be utilized to separate tissue along natural tissue separation lines or cleavage surfaces by nudging the tissue with the tissue separating tip of the surgical tissue separator. In accordance with the invention, should a surgeon apply too much pressure in attempting to separate tissue the flexible stem of the surgical tissue separator will bend providing a tactile and visual indication of the use of excessive pressure in separating the tissue. Controlled flexibility is achieved while precisely measuring tissue resistance.

BRIEF DESCRIPTION OF THE DRAWINGS

FIG. 1 is a partially broken away longitudinal elevation view of a manual surgical tissue separator constructed in accordance with the invention in a straight configuration.

FIG. 2 is an enlarged section view of the surgical tissue separator structure illustrated in FIG. 1 taken substantially on the line 2—2 in FIG. 1.

FIG. 3 is a partial longitudinal section view of the surgical tissue separator structure illustrated in FIG. 1 taken substantially on the line 3—3 in FIG. 1.

Different types of adjacent tissues (i.e. skin to muscle, tendon to bone, peritoneum to muscle, etc.) resist differently in response to instrument pressure thus creating a natural cleavage plane at their interface. Thus, tissue separation at the cleavage surface is possible and preferable to incising or tearing elsewhere. The tissue surgical separator of the present invention is also intended to be used within the cleavage planes as described in the foregoing.

FIG. 4 is an elevation view of a modified stem and tip structure in a double bend configuration for use in the surgical tissue separator illustrated in FIG. 1.

FIG. 5 is an elevation view of another modification of the stem and tip structure of the surgical tissue separator illustrated in FIG. 1 in a single bead configuration.

FIG. 6 is an elevation view of still another modification of the stem and tip structure of the surgical tissue separator illustrated in FIG. 1 in a right angle bend configuration.

FIG. 7 is a partial section view of a mold utilized in forming the tips of the surgical tissue separator structure of FIG. 1 in accordance with the method of the invention.

FIG. 8 is a partial section view of the mold structure illustrated in FIG. 7 with removable mold portions or cores in position and prior to molding of tips in the mold structure.

FIG. 9 is a section view of the mold structure of FIG. 8 taken substantially on the line 9—9 in FIG. 8.

FIG. 10 is a partial section view of the mold structure utilized to form the tips of the surgical tissue separator as illustrated in FIG. 1 showing the tips formed and the working ends of the stems molded directly in the tips.

DESCRIPTION OF THE PREFERRED EMBODIMENT

As shown best in FIG. 1, the surgical tissue separator or nudger 10 comprises an elongated shaft 12 having a ball tip 14 secured to the stem end thereof. Shaft 12 is divided into a handle 16 and a stem 18.

In use, the handle 16 is held by a surgeon and the tip 14 is manipulated in contact with tissue to be separated. The tissue to be separated is thus separated or nudged away along natural separation lines or cleavage surfaces.

More specifically, the handle 16 as shown best in FIG. 1 is an elongated cylindrical member. If removable as shown the handle 16 has a reduced diameter threaded portion 20 at the lower end thereof adapted to be threadably engaged by the stem 18 to secure the stem 18 to the handle 16. One or both sides of the handle 16 may be provided with a flattened portion 22 on which the surgeon's name and nudger model identification or the like may be inscribed.

While the handle 16 may be constructed of any of a number of materials, desirably the handle 16 is rigid and may be constructed of stainless steel having a satin finish. While dimensioning of the handle is of no great importance to provide proper feel and weight, a handle approximately four inches long overall and one-quarter of an inch in diameter has been found to be within the desirable range.

Also, the handle 16 may be of different color in accordance with the invention to designate different stem dimensions in accordance with the invention. Thus the color of the handle 16 may provide an indication of the flexibility of the stem associated therewith so that in use the surgical tissue separator may be called for by handle color.

The stem 18 as shown in FIG. 1 is substantially straight and is slightly conical with the smaller diameter being near the tip. Stem 18 has threaded recess 24 in the upper end thereof for receiving the threaded reduced diameter portion 20 of the handle 16.

The stem 18 as shown in FIG. 1 is approximately 4.7 inches long and is tapered from a diameter of approximately 0.15 inches at point 26 to a diameter of approximately 0.08 inches at point 28 which is approximately three inches below point 26. The remainder of the stem 18 to the tip 14 is then of a standard diameter of approximately 0.08 inches.

The stem 18 may be made of a plurality of different materials. However, it is desirable for the stem 18 as shown in FIG. 1 to be flexible. Stem 18 is therefor in a preferred embodiment molded of "ABS" or polycarbonate plastic. The stem 18 is preferably, but not necessarily, black. It is desirable that the stem is of a color contrasting with the color of the handle 16 and the tip 14.

Tip 14 best shown in FIG. 3, is generally spherical and is provided with a recess 30 therein for receiving the tip 32 of the stem 18. The tip 32 of the stem 18 is provided with radially extending projections 34 and 36 on opposite sides thereof which fit into radially extending recesses 38 and 40 within the axially extending recess 30 in the tip 14 as shown in FIG. 3.

The tip 14 may also be of a plurality of different non-stick materials and in a preferred embodiment is molded of "TEFLON" which is a polytetroflunoethylene obtainable from the DuPont Corporation.

As shown best in FIG. 3, the tip 14 may be snapped over the end 32 of the stem 18 in an interference fit. The projections 34 and 36 are sufficient to retain the tip 14 on the end 32 of the stem 18. However, if added security is desired adhesive 39 may be placed in the recess 30 to further secure the tip 14 to the end 32 of stem 18.

Alternatively, the tip 14 may be first molded of "TEFLON". The stem 18 may then subsequently be molded with the tip 14 being utilized as an insert in the mold for molding the stem 18 whereby the stem 18 is molded within the end 32 thereof positioned within the tip 14 as will be considered later in conjunction with FIGS. 7 through 10. When the stem 18 is molded in position in the tip 14, the preferably spheroidal tip 14 is constructed of "TEFLON" which has a higher melting point than the stem 18 which is constructed of "ABS" which is an acrylonitrile-butadiene-styrene copolymer manufactured by Union Carbide Corporation, Borg Warner Company and others.

Furthermore, the material of which the spheroidal tip 14 is constructed is preferably of a color contrasting to both the color of all of the stem, which as pointed out above is black in a preferred embodiment, the handle, which as also set forth above, may be color coded to indicate flexibility of an associated stem and the red or whitish tissue material. Thus, the tip 14 may preferably be bright yellow and luminescent to assure location thereof and assessment of depth thereby by the surgeon.

Stem 18 may take many configurations other than straight as shown in FIG. 1, as shown by the stems 42, 44, and 46 illustrated in FIGS. 4, 5 and 6. The double bend or curved stem 42 is first angled with respect to the axis of the stem 42 at approximately 25° and then is returned at a 90° angle as shown in FIG. 4.

The single bend stem 44 includes the end portion 52 which is at approximately 25° with respect to the longitudinal axis of the rest of the stem 44 as shown in FIG. 5.

The right angle stem 46 shown in FIG. 6 includes the end 54 extending at right angles to the longitudinal axis of the rest of stem 46.

Stems 42, 44 and 46 are of approximately the same size as the stem 18 and all of the stems are molded of "ABS" plastic in the preferred embodiment.

In overall use of the surgical separator or nudger 10, with one of the stems 18, 42, 44 and 46 secured to the handle 16, a surgeon grips the handle 16 and manipulates the tip 14 in contact with tissue to be separated. Tissue is thus separated along natural separation lines. If necessary, two or more nudgers can be used depending on personal desirability.

Should the surgeon use an undesirable amount of force in attempting to separate tissue, the flexible stem 18 will bend to provide the surgeon with a visual and tactile indication of the use of undesirable force in separating the tissue so that the nudgers may relieve the pressure in time. This relationship which varies with resistance of the tissues and the size of the nudger, establishes through use a built in response as is common with other tools or manual equipment used by men such as a pencil and lead for example. As set forth above, to allow quick selection of nudger size during a surgical procedure, the nudgers may have color coded handles for insured quick identification by the surgeon and his assistants.

In a preferred example, utilizing the stem 18, sized as indicated above, the flexibility of stem 18 is such that a three ounce force applied vertically through the geometrical center of the spheroidal tip 14 with the handle held rigidly at an angle of 30° to the horizontal tissue surface being contacted by the spheroidal tip, immediately adjacent the stem, will produce vertical movement of the tip 14 of approximately 1/16 of an inch which can readily be seen and sensed by the surgeon.

While the exact flexibility of the stems 18, 42, 44 and 46 is not essential to the invention, it should be understood that in order to implement the feature of the invention utilizing the flexible stems 18, 42, 44 and 46, it is necessary that the flexibility of the stems be such as to provide both a visual and tactile indication of excessive force utilized in separating or nudging tissue before irreversible damage due to tearing or crushing takes place.

The following more complete range of working relationships exist between vertical forces applied centrally against the tip 14 with the handle held rigidly at an angle of 30° to a horizontal tissue surface being contacted by the spheroidal tip and vertical movement of the tip 14 produced by the forces due to flexure of the stem with the stem 18 constructed of "ABS" and sized as indicated above.

| force (in oz.) | movement of tip (in.) |
| --- | --- |
| 0 | 0 |
| 1.5 | 1/32 |
| 3.0 | 1/16 |
| 4.5 | 3/32 |
| 5.5 | ⅛ |

In another embodiment of the invention also constructed of "ABS" with a straight tip as shown in FIG. 1 having diameters at points 26 and 28 of 0.140 inches and 0.125 inches respectively the relationship between such vertical forces and vertical movement of the tip due to flexure of the stem were as follows.

| force (in oz.) | movement of tip (in.) |
| --- | --- |
| 0 | 0 |
| 5.0 | ⅛ |
| 9.5 | ⅛ |
| 18.0 | ⅛ |

With the stem constructed of "ABS" and bent as shown in FIG. 5 and having diameters of 0.075 inches and 0.040 inches at the points indicated above the relationship between vertical forces applied and movement of the tip 14 due to flexure of the stem approximately as follows.

| force (in oz.) | movement of tip (in.) |
| --- | --- |
| 0 | 0 |
| .5 | 1/64 |
| stem too flexible to provide reading | 1/32 |

With the stem again constructed of "ABS" and having the configuration shown in FIG. 5 and having diameters of 0.150 and 0.080 at the points indicated above the relationships between vertical forces applied and movement of the tip 14 due to flexure of the stem were as follows.

| force (in oz.) | movement of tip (in.) |
| --- | --- |
| 0 | 0 |
| 1.0 | 1/32 |
| 3.0 | 1/16 |
| 4.0 | 3/32 |
| 4.8 | ⅛ |

With the stem constructed of "ABS" and having the configuration shown in FIG. 4 and having diameters of 0.075 and 0.040 at the points indicated above, the relationships between vertical forces applied and movement of the tip 14 due to flexure and the stem were as follows.

| force (in oz.) | movement of tip (in.) |
| --- | --- |
| 0 | 0 |
| 1.0 | 1/64 |
| 1.75 | 1/32 |
| stem too flexible | 1/16 |

| force (in oz.) | movement of tip (in.) |
| --- | --- |
| to provide reading | |

As indicated above, flexible tips 18, 42, 44 and 46 must be constructed of some material such as "ABS" plastic which will return to its original position after the force upon the tip has been removed, providing the stem has not been deformed beyond its plastic limit or through excessive exposure to heat.

In use the surgical separator structure 10 provides a preferred method of separating tissue by mechanical nudging to separate the tissue along natural separation lines or cleavage surfaces. Such tissue separation is readily accomplished without severing or crushing tissue as with a scalpel, scissors, forceps or the like. Such tissue separation produces less trauma to surrounding tissue and draws less blood. The tissue separating structure 10 has thus been utilized in accordance with the method of the invention to, for example, separate small tumors and their natural sac from healthy surrounding tissue with success in that the tumors were readily separated with a minimum of trauma to surrounding tissue and very little bleeding.

As pointed out above, the tip 14 may be secured to the stem 18 by molding the tip 14 and subsequently molding the stem 18 with the tip 14 being utilized as an insert in the mold for molding the stem 18. Such method of securing the tip 14 to the stem 18 is illustrated in FIGS. 7 through 10.

As shown in FIG. 7, a multi-cavity mold 56 is provided having cavities 58 therein into which "TEFLON" may be injected through the sprues 60.

To provide the recesses 38 and 40 in the tips 14, the tips 14 are injection molded with cores 62, 64 and 66 in the mold 56. As shown best in FIGS. 8 and 9, the cores 62 and 66 are generally rectangular in cross-section and have radially extending projections 68 and 70 thereon which are substantially triangular in cross-section as shown in FIG. 8. The core 64 is generally cylindrical and has the longitudinally extending recesses 72 and 74 therein for receiving the cores 62 and 66.

Because of the particular shape of the cores 62, 64 and 66 the cores may be inserted in the mold 56 and withdrawn therefrom without stripping the tips 14 from the mold 56. Thus, in operation, the cores 62 and 66 are first positioned as shown best in FIG. 7 and the core 64 is later placed in the position as shown in FIG. 7 to lock the cores 62 and 66 in position. The reverse procedure is utilized in removing the cores 62, 64 and 66 from the mold 56.

After pouring the tips 14 in the mold 56 through the sprues 60 with the cores 62, 64 and 66 in place, the cores 62, 64 and 66 are removed and the stems 18 are molded by pouring through sprues not shown with the tips 14 still in place in the mold 56 as shown in FIG. 10.

The "ABS" of the stems 18 having a lower melting point than the "TEFLON" of the tips 14 permits the subsequent pouring of the stems 18 whereby as a finished product the tips 14 are molded in place on the stems 18.

While one embodiment of the present invention has been considered in detail, it will be understood that other embodiments and modifications thereof are contemplated by the inventor. It is the intention to include all the embodiments and modifications as are defined by the appended claims within the scope of the invention.

I claim:

1. Surgical separator structure comprising an elongated shaft constructed of a non-helical shaped member extending straight in the direction of elongation for most of its length including a handle at one end, a transversely directionally universally, easily flexed other end, and a tip at the other end for displacing or separating tissue on contact therewith.

2. Structure as set forth in claim 1 wherein the tip is a separate member in the shape of a spheroid having a dimension transverse to the longitudinal axis of the shaft substantially larger than the transverse dimension of the adjacent portion of the other end of the shaft and the shaft and tip further include means for snapping the tip onto the other end of the shaft.

3. Structure as set forth in claim 2 wherein the means for snapping the tip on the other end of the shaft comprises projections on the other end of the shaft extending radially therefrom, a recess in the tip for receiving the other end of the shaft, and radially extending recesses in the tip within the recess in the tip complimentary to the projections on the other end of the tip for receiving the projections on the other end of the tip.

4. Structure as set forth in claim 3 and further including adhesive between the other end of the shaft and the tip for securing the tip to the other end of the shaft.

5. Structure as set forth in claim 1 wherein the shaft includes a substantially rigid handle portion and a stem portion and means operable between the handle portion and one end of the stem portion for securing the handle portion and the stem portion together and wherein the tip is secured to the other end of the stem portion of the shaft and is in the shape of a spheroid having a dimension transverse to the longitudinal axis of the shaft substantially larger than the transverse dimension of the adjacent portion of the other end of the shaft.

6. Structure as set forth in claim 5 wherein the entire stem portion of the shaft is transversely, directionally, universally easily flexed.

7. Structure as set forth in claim 6 wherein the stem portion of the shaft is straight over its entire length.

8. Structure as set forth in claim 6 wherein the stem portion of the shaft has a double bend at the other end thereof.

9. Structure as set forth in claim 6 wherein the stem portion of the shaft has a single bend at the other end thereof so as to extend obliquely to the axis of extent of most of the length of the stem portion at the other end thereof.

10. Structure as set forth in claim 6 wherein the stem portion of the shaft is terminated in a short portion extending at right angles thereto at the other end thereof.

11. Structure as set forth in claim 5 wherein the handle portion of the shaft is color coded to provide a visual indication of the flexibility of the stem portion of the shaft.

12. Structure as set forth in claim 5 wherein the tip is colored, a color contrasting to the color of the stem and the red or whitish color of tissue for facilitating location of the tip and/or depth assessment of the tip.

13. Structure as set forth in claim 5 wherein the tip is luminescent.

14. Structure as set forth in claim 5 wherein the tip is constructed of "TEFLON" and the stem is constructed of "ABS".

15. Structure as set forth in claim 1 wherein the non-helical shaped member is solid.

16. Surgical separator structure comprising a generally cylindrical, relatively rigid handle portion, one end of which is reduced in diameter and is threaded to receive one end of a slender and relatively flexible stem portion, a stem portion which is molded of "ABS" and has a progressively smaller diameter from the one end to the other thereof so as to be transversely directionally universally, relatively easily flexed, an axially extending threaded recess in the one end of the flexible stem portion, projections on the other end of the flexible stem portion extending radially therefrom for securing a tip to the other end of the stem portion, a spheroidal tip molded of Teflon or equivalent low friction material on the other end of the flexible stem portion including a recess therein for receiving the other end of the stem portion and radially extending recesses in the tip within the recess in the tip complementary to the projections on the other end of the stem portion for receiving the projections with the tip in assembly on the other end of the flexible stem portion whereby the tip may be snapped on to the stem portion and an adhesive between the tip and other end of the flexible stem portion for securing the tip in place on the other end of the stem portion.

17. Surgical separator structure comprising an elongated shaft including a substantially rigid handle portion at one end extending for substantially half the length of the shaft, one end of which is threaded, and a stem portion extending longitudinally for approximately half the length of the shaft having a recess in one end which is threaded complementary to the threaded end of the handle, whereby the stem portion and the handle portion may be secured together with the one end of the handle extending into the recess in the one end of the stem, said stem being slightly tapered from a larger diameter at the one end to a smaller diameter at the other end and being solid and straight over most of its length and being transversely directionally universally, easily flexible, and a spherical ball secured to the other end of the stem portion having a dimension transverse to the longitudinal axis of the shaft substantially larger than the transverse dimension of the adjacent portion of the other end of the shaft, whereby in use with the surgical separator structure held by the handle living tissue may be separated on engagement of the spherical ball with the tissue with a predetermined force depending on the displacement of the ball from the longitudinal axis of the shaft on flexure of the stem portion.

18. Structure as set forth in claim 17 wherein the other end of the stem portion adjacent the shaft is one of straight, has a double bend at the other end thereof, has a single bend at the other end thereof so as to extend obliquely to the axis of extent of most of the length of the stem portion at the other end thereof, and is terminated in a short portion extending at right angles thereto at the other end thereof.

19. Structure as set forth in claim 18 wherein the handle portion of the shaft is color coded to provide a visual indication of the flexibility of the stem portion of the shaft, the tip is colored in a color contrasting to the color of the stem and the red or whitish color of tissue for facilitating location of the tip and or depth of the tip and is luminescent, and wherein the tip is constructed of TEFLON and the stem is constructed of ABS.

* * * * *